(12) United States Patent
Brimhall (10) Patent No.: US 7,691,093 B2
(45) Date of Patent: Apr. 6, 2010

(54) METHOD OF AND APPARATUS FOR CONTROLLING FLASHBACK IN AN INTRODUCER NEEDLE AND CATHETER ASSEMBLY

(75) Inventor: Greg L. Brimhall, West Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/484,687

(22) PCT Filed: Jun. 20, 2003

(86) PCT No.: PCT/US03/19667

§ 371 (c)(1), (2), (4) Date: Jan. 23, 2004

(87) PCT Pub. No.: WO04/000407

PCT Pub. Date: Dec. 31, 2003

(65) Prior Publication Data

US 2005/0015071 A1 Jan. 20, 2005

Related U.S. Application Data

(60) Provisional application No. 60/390,349, filed on Jun. 21, 2002.

(51) Int. Cl.
*A61M 31/00* (2006.01)

(52) U.S. Cl. .................................................. 604/506

(58) Field of Classification Search ............ 604/165.03, 604/168.01, 165.02, 256, 260, 164.02, 164.06, 604/166.01, 167.06, 207, 246
See application file for complete search history.

(56) References Cited

U.S. PATENT DOCUMENTS

| 4,755,170 A | 7/1988 | Golden | 604/52 |
|---|---|---|---|
| 4,810,248 A | 3/1989 | Masters et al. | 604/192 |
| 4,816,024 A | 3/1989 | Sitar et al. | 604/192 |
| 4,832,696 A | 5/1989 | Luther et al. | 604/164 |
| 4,834,718 A | 5/1989 | McDonald | 604/195 |
| 4,846,811 A | 7/1989 | Vanderhoof | 604/263 |
| 4,894,052 A * | 1/1990 | Crawford | 604/507 |
| 4,917,669 A | 4/1990 | Bonaldo | 604/164 |
| 4,929,241 A | 5/1990 | Kulli | 604/263 |

(Continued)

FOREIGN PATENT DOCUMENTS

| EP | 0 750 916 A2 | 1/1997 |
| EP | 0 747 083 A3 | 4/1997 |
| EP | 0 747 085 A3 | 4/1997 |
| GB | 2 343 118 A | 9/1999 |
| WO | WO 98/19725 | 5/1998 |
| WO | WO 99/08742 | 2/1999 |

*Primary Examiner*—Nicholas D Lucchesi
*Assistant Examiner*—Christopher D Koharski
(74) *Attorney, Agent, or Firm*—Mony R. Ghose; Craig Metcalf; Kirton & McConkie (57) ABSTRACT

A method is provided for controlling the fluid flow rate in an extension tube of an introducer needle assembly for use as confirmation flashback. The introducer needle assembly has a catheter attached to a catheter hub with a side port, an extension tube attached to the side port on the catheter hub, and an introducer needle with a notch adapted to be inserted into a bore in the catheter. A lumber extends through the needle and is in fluid communication with the notch. The needle has an outer diameter smaller than the diameter of the bore such that an annular space is defined between the catheter and the needle. The fluid, typically blood, is at a pressure and has a viscosity when the needle accesses it. A preferred minimum fluid velocity of the fluid through the extension tube is selected (preferably at least 1 inch per minute though the extension tube in certain applications). The notch and the annular space are sized based, at least in part, on the viscosity of the fluid and the pressure of the fluid to achieve the preferred flow rate though the extension tube.

15 Claims, 6 Drawing Sheets

U.S. PATENT DOCUMENTS

| | | | |
|---|---|---|---|
| 4,944,725 A | 7/1990 | McDonald | 604/164 |
| 4,964,854 A | 10/1990 | Luther | 604/166 |
| 4,966,586 A | 10/1990 | Vaillancourt | 604/164 |
| 4,978,344 A | 12/1990 | Dombrowski et al. | 604/198 |
| 4,994,041 A | 2/1991 | Dombrowski et al. | 604/164 |
| 5,049,136 A | 9/1991 | Johnson | 604/198 |
| 5,051,109 A | 9/1991 | Simon | 604/263 |
| 5,053,017 A | 10/1991 | Chamuel | 604/192 |
| 5,085,648 A | 2/1992 | Purdy et al. | 604/198 |
| 5,135,504 A | 8/1992 | McLees | 604/164 |
| 5,147,327 A | 9/1992 | Johnson | 604/198 |
| 5,176,655 A | 1/1993 | McCormick et al. | 604/198 |
| 5,186,712 A | 2/1993 | Kelso et al. | 604/165 |
| 5,215,525 A | 6/1993 | Sturman | 604/164 |
| 5,215,528 A | 6/1993 | Purdy et al. | 604/164 |
| RE34,416 E | 10/1993 | Lemieux | 604/164 |
| 5,259,587 A * | 11/1993 | D'Alessio et al. | 251/4 |
| 5,279,591 A | 1/1994 | Simon | 604/263 |
| 5,300,045 A | 4/1994 | Plassche, Jr. | 604/263 |
| 5,312,359 A | 5/1994 | Wallace | 604/164 |
| 5,322,517 A | 6/1994 | Sircom et al. | 604/198 |
| 5,328,480 A | 7/1994 | Melker et al. | 604/164 |
| 5,328,482 A | 7/1994 | Sircom et al. | 604/164 |
| 5,395,347 A | 3/1995 | Blecher et al. | 604/198 |
| 5,409,461 A | 4/1995 | Steinman | 604/110 |
| 5,458,658 A | 10/1995 | Sircom | 60/192 |
| 5,558,651 A | 9/1996 | Crawford et al. | 604/263 |
| 5,562,633 A | 10/1996 | Wozencroft | 604/171 |
| 5,573,510 A | 11/1996 | Isaacson | 604/158 |
| 5,584,809 A | 12/1996 | Gaba | 604/110 |
| 5,599,310 A | 2/1997 | Bogert | 604/164 |
| 5,601,536 A | 2/1997 | Crawford et al. | 604/263 |
| 5,611,781 A | 3/1997 | Sircom et al. | 604/164 |
| 5,613,952 A | 3/1997 | Pressly, Sr. et al. | 604/110 |
| 5,662,610 A | 9/1997 | Sircom | 604/110 |
| 5,676,658 A | 10/1997 | Erskine | 604/263 |
| 5,695,474 A | 12/1997 | Daugherty | 604/162 |
| 5,697,907 A | 12/1997 | Gaba | 604/110 |
| 5,697,914 A | 12/1997 | Brimhall | 604/177 |
| 5,704,919 A | 1/1998 | Kraus et al. | 604/192 |
| 5,713,876 A | 2/1998 | Bogert et al. | 604/243 |
| 5,718,688 A | 2/1998 | Wozencrot | 604/164 |
| 5,810,780 A * | 9/1998 | Brimhall et al. | 604/167.02 |
| 5,833,670 A | 11/1998 | Dillon et al. | 604/263 |
| 5,853,393 A | 12/1998 | Bogert | 604/165 |
| 5,865,806 A | 2/1999 | Howell | 604/164 |
| 5,879,337 A | 3/1999 | Kuracina et al. | 604/192 |
| 5,882,337 A | 3/1999 | Bogert et al. | 604/110 |
| 5,911,705 A | 6/1999 | Howell | 604/110 |
| 5,935,109 A | 8/1999 | Donnan | 604/164 |
| 5,951,515 A | 9/1999 | Osterline | 604/110 |
| 6,001,080 A | 12/1999 | Kuracina et al. | 604/171 |
| 6,012,213 A | 1/2000 | Chang et al. | 29/447 |
| 6,042,567 A | 3/2000 | McNamara | 604/168 |
| 6,221,050 B1 | 4/2001 | Ishida | 604/167.03 |
| 6,506,181 B2 | 1/2003 | Meng et al. | 604/164.07 |
| 2001/0041871 A1 | 11/2001 | Brimhall | 604/167.02 |
| 2001/0056275 A1 | 12/2001 | Brushey | 604/525 |
| 2002/0007152 A1 | 1/2002 | Hermann et al. | 604/167.04 |
| 2002/0055716 A1 | 5/2002 | Nakagami | 604/164.12 |
| 2002/0107483 A1 | 8/2002 | Cook | 604/164.01 |
| 2002/0177816 A1 | 11/2002 | Brimhall et al. | 604/174 |

* cited by examiner

METHOD OF AND APPARATUS FOR CONTROLLING FLASHBACK IN AN INTRODUCER NEEDLE AND CATHETER ASSEMBLY

CROSS-REFERENCES TO RELATED APPLICATIONS

This application is a 371 of PCT US/03/19667 filed Jun. 20, 2003 which claims the benefit of provisional application 60/390,349 filed Jun. 21, 2002.

FIELD OF THE INVENTION

This invention relates to the field of catheter and introducer needle assemblies. Specifically, the invention relates to a method of and an apparatus for controlling flashback in an introducer needle and catheter assembly.

BACKGROUND OF THE INVENTION

Catheters, particularly intravenous (IV) catheters, are used for directing fluid into or withdrawing fluid from a patient. The most common type of IV catheter is an over-the-needle IV catheter. As its name implies, an over-the-needle IV catheter is mounted over an introducer needle having a sharp distal tip. With the distal tip of the introducer needle extending beyond the distal tip of the IV catheter, the assembly is inserted through the patient's skin into a vein. Once placement of the assembly in the vein is verified by flashback of blood in the needle, the needle is withdrawn, leaving the IV catheter in place. In certain circumstances, the caregiver may move the needle within the vein, or may displace the catheter with respect to the needle, to locate the catheter in a desired position before fully withdrawing the needle. The proximal end of the IV catheter typically has a hub that is designed to be connectable to an IV fluid supply line after insertion of the IV catheter in a patient. In other applications, an IV set (known as an "extension set") is attached before insertion into the patient.

Although typical IV catheter and introducer needle assemblies generally perform their functions satisfactorily, they do have certain drawbacks. For example, certain IV catheter and introducer needle assemblies typically require a flashback chamber located on the proximal end of the needle. This location is inconvenient for the healthcare worker because, during insertion of the assembly into a patient, the healthcare worker's attention is directed to the distal tip of the needle. Thus, in order to determine if the needle is properly placed in a vein, the healthcare worker has to divert his attention away from the point of insertion of the IV catheter and introducer needle assembly into the patient. Even in devices that permit visual confirmation of flashback at a location near the needle tip, there is no distinct confirmation that the needle remains in the vein as it is positioned by the caregiver. Typically, flashback chambers are immediately filled with blood upon the initial access of the vein and cannot be used to confirm that the catheter assembly has maintained (or achieved again) access to the vein.

SUMMARY OF THE INVENTION

It is therefore an object of one aspect of this invention to provide a method for controlling the flashback rate in an extension tube.

It is an object of another aspect of the invention to provide a method of making an introducer needle and catheter assembly that includes a controlled, visible flashback rate in an extension tube. Specifically, catheter assembly may be designed to achieve initial flashback at the needle tip, as well as distinct confirmation flashback at a controlled rate when the catheter is located within the patient's vein.

It is an object of another aspect of the invention to provide an introducer needle assembly that permits initial flashback at the needle tip, as well as distinct confirmation flashback at a controlled rate when the needle assembly is located within the patient's vein.

It is an object of another aspect of this invention to provide a method of inserting a catheter into a patient's vein that permits initial flashback at the needle tip, as well as distinct confirmation flashback at a controlled rate over a predetermined period of time while the catheter is located within the patient's vein.

In accord with one aspect of the invention, a method is provided for controlling the fluid flow rate in an extension tube of an introducer needle assembly for use as confirmation flashback. The introducer needle assembly has a catheter attached to a catheter hub with a side port. An extension tube is attached at one end to the side port on the catheter hub. The other end of the extension tube is plugged with a porous material that permits air to pass but restricts liquid flow. An introducer needle with a notch is adapted to be inserted into a bore in the catheter. A chamber extends through the needle and is in fluid communication with the notch. The needle has an outer diameter smaller than the diameter of the catheter bore such that an annular space is defined between the catheter and the needle. The liquid or fluid, typically blood, is at a pressure and has a viscosity when the needle accesses it. A fluid flow path is created from the patient's blood vessel, through the needle tip and through center of the hollow needle, through the notch in the needle to the annular space, along the annular space to the catheter hub and out the side port, and into the extension tube.

In use, the caregiver inserts the introducer needle and catheter assembly into the patient's vein. During insertion of the assembly, the notch is maintained within the catheter. An initial flashback is visible near the tip of the translucent catheter (and thus near the point of insertion) as blood flows through the notch and into the annular space. As the blood continues to flow, it passes through to the extension tube where the caregiver can observe the flow of blood in the extension tube (confirmation flashback) at a controlled rate (referred to herein as the "visual flow front rate"), as discussed below.

During design of the introducer needle and catheter assembly, the geometry and materials of the assembly are selected to achieve a desired visual flow front rate through the extension tube. Particularly, it is desirable to control the flow rate such that confirmation flashback occurs for a relatively long period of time, permitting the caregiver to know for a longer period of time that the tip of the catheter is within and in fluid communication with the vein, as well as to understand the nature of the blood vessel accessed. In one implementation of the instant invention for use in connection with an integrated catheter assembly (that is, a catheter assembly including an extension tube attached to the catheter hub before insertion) intended for vascular access, a desired minimum fluid flow rate of the fluid visible through the extension tube (that is, the visual flow front rate) is selected to be around 1 inch per minute. The determination is then made as to which component of the catheter assembly is to be employed as the "throttle," that is, the controlling element in the catheter assembly. The geometry (and materials, in certain circumstances) can then be designed to achieve the desired visual flow front rate.

In another implementation of the invention, the notch and the annular space are sized so that the size of the central chamber within the needle acts as the throttle. Specifically, both the notch and the annular space are designed to have cross-sectional areas greater than the cross sectional area of the chamber running through the needle. Consequently, the needle chamber acts as the throttle. In the case of a 20 gauge needle, the needle chamber has a diameter of 0.016 inches and a cross sectional area of about 0.00020 in$^2$ (that is, $\pi*0.008^2=0.0002$ in$^2$). The annular space and the notch are sized appropriately to have larger cross sectional areas. A 20 gauge needle has an outer diameter of 0.028 inches. A catheter appropriate for such a needle would be an 18 gauge catheter which has a bore with a diameter of 0.034 inches. Consequently, the annular space has a cross sectional area of about 0.0003 square inches. The notch is also sized to have a minimum area greater than the needle's central chamber. In the case of a notch formed by grinding out a straight-sided opening in the needle wall (resulting in a rectangular notch) through to the center of the needle, the notch has a width equal to the diameter of the needle chamber (i.e., 0.016 inches). The notch length in the axial direction is selected to be equal to or greater than the cross-sectional area of the chamber divided by the diameter of the chamber. Consequently, in this case, the length is preferably at least 0.0125 inches (that is, 0.0002 inches$^2$/0.016 inches=0.0125 inches).

In such an assembly, the extension tube may be selected to have an internal diameter of 0.05 inches, resulting in a cross-sectional area of about 0.002 in. When used for peripheral vascular access, the fluid is at a pressure between 10 mmHg-250 mmHg is (typically about 45 mmHg) and has a viscosity of about 1.8 times that of water at normal body temperature of 98.6° F. when the needle tip accesses it. The visual flow front rate is then typically about 1 inch per minute through the extension tube. Different blood pressure and blood viscosity will affect the visual flow front rate.

In other implementations, it is desirable to size the annular space between the needle and the catheter (based, at least in part, on the viscosity of the fluid and the pressure of the fluid) to act as a throttle, restricting (and thereby controlling) the flow through the flow path and achieving the preferred flow rate through the extension tube. Alternatively, the notch may be sized such that it acts as the throttle. Further, the porosity of the plug in the extension tube may be designed such that it permits air to flow out of the tube at a rate which acts as a throttle by preventing the blood from entering the tube any faster.

In accord with aspects of certain implementations of the instant invention, an integrated introducer needle and catheter assembly is provided including a controlled flow rate through the extension tube. A flow path is created by the introducer needle assembly from the vein to the extension tube. The flow path extends from the tip of the needle, through the needle chamber, through the notch, into and along the annular space between the needle and the catheter, and then into the central chamber of the extension tube via a catheter hub. The porous plug permits air in the extension tube to pass out as the chamber fills with blood. The geometry and material properties of the assembly are selected to achieve a desired visual flow front rate in the extension tube which can be observed by a caregiver but which does not restrict flow in a manner that would interfere with the delivery of fluids by the assembly after insertion. Currently, it is preferred that the flow rate be selected such that the extension tube fills at a rate of at least 1 inch per minute, but other rates may be desirable depending on the application. Further, it will be appreciated that various modifications of the geometry and material properties may be employed and still practice aspects of the invention.

In accord with another aspect of the invention, a method of accessing a blood vessel is provided. An introducer needle assembly has a catheter attached to a catheter hub with a side port, an extension tube attached to the side port on the catheter hub, and an introducer needle with a notch adapted to be inserted into the catheter. The tip of the introducer needle is inserted into the blood vessel thereby positioning the tip of the catheter in the blood vessel as well. Insertion of the introducer needle in the blood vessel is confirmed by observing blood in the catheter near the notch. The positioning of the needle tip in the blood vessel is further confirmed by observing blood flow through the extension tube. The visual fluid flow front rate of blood through the extension tube is a predetermined rate based upon, at least in part, the size of the notch, the size of the internal bore of the catheter and the outer diameter of the needle. Additionally or alternatively, the flow rate is controlled based, at least in part, on the pressure of the blood and the viscosity of the blood, and on the internal cross section of the extension tube.

In accord with yet another aspect of the invention, a method is provided for controlling flashback in an extension tube of an introducer needle assembly. A translucent catheter is provided having a proximal end, a distal end and a central bore extending from the proximal end to the distal end. A catheter hub is in fluid communication with the central bore and has a proximal end and a distal end connected to the proximal end of the catheter and a side port in fluid communication with the catheter hub. An extension tube is in fluid communication with the side port. The proximal end of an introducer needle extends from the distal end of a needle hub. The introducer needle adapted to be positioned within the catheter in an insertion position wherein the distal end of the introducer needle extends distally past the distal end of the catheter. A seal is affixed to the catheter hub and located proximal of the side port, sealing the proximal end of the catheter hub. The introducer needle has a cross sectional area that is less than the cross sectional area of the central bore such that an annular space is defined between the introducer needle and the catheter. A notch at the distal end of the introducer needle is located within the catheter when the introducer needle is in the insertion position such that fluid can communicate between the notch at the distal end of the introducer needle and the side port but is prevented from passing out of the proximal end of the catheter hub by the seal. The introducer needle, the notch and the central bore are sized to control the flow of fluid through the annular space, thereby controlling the flow of fluid through the extension tube.

BRIEF DESCRIPTION OF THE DRAWINGS

The above and other objects and advantages will be apparent upon consideration of the following drawings and detailed description. The preferred embodiments of the present invention are illustrated in the appended drawings in which like reference numbers refer to like elements and in which.

DETAILED DESCRIPTION OF THE INVENTION

Figure 1:
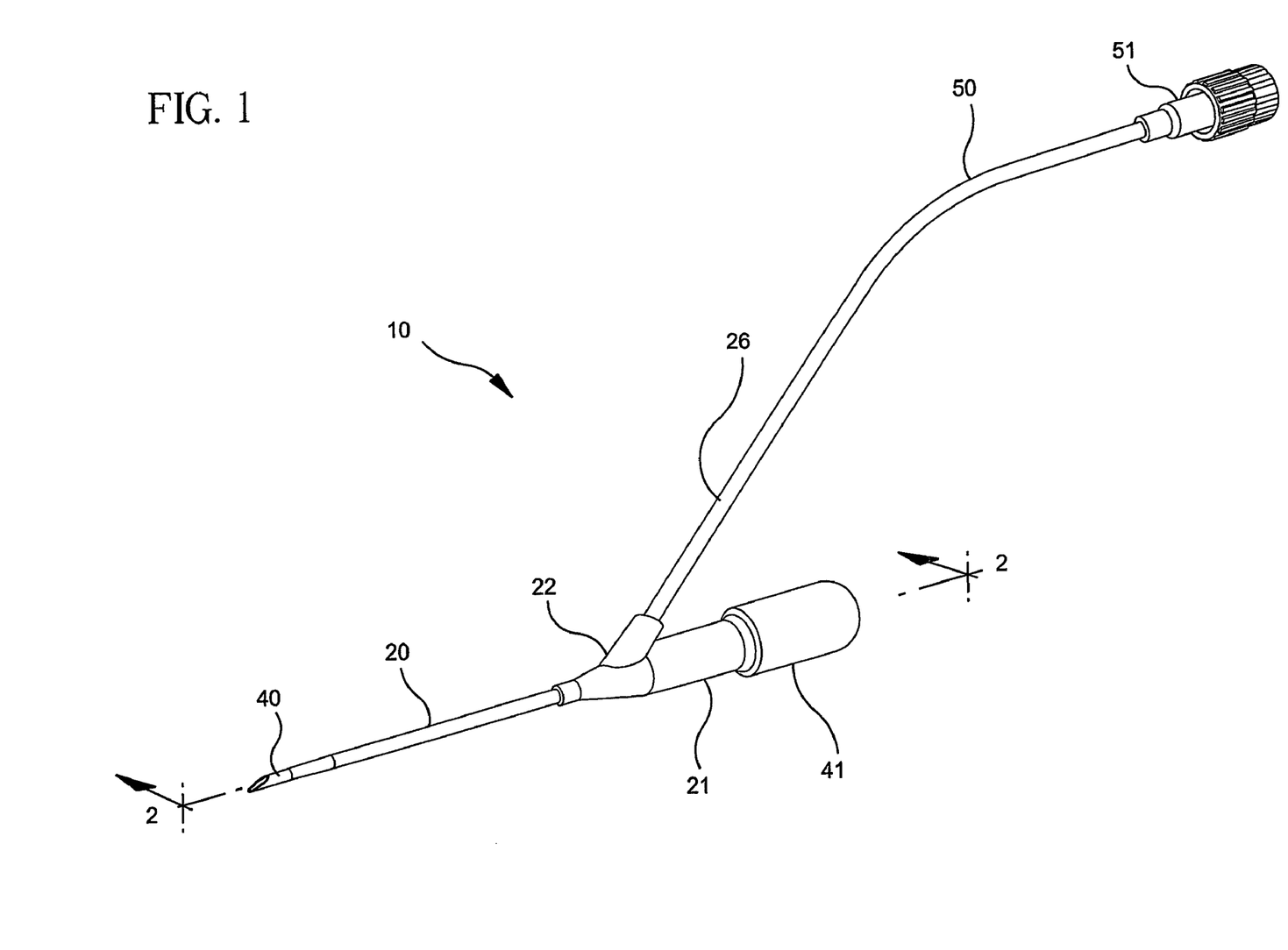
FIG. 1 is a perspective view of the IV catheter and introducer needle in accord with an aspect of the invention.

The catheter and introducer needle assembly 10 in accord with one implementation of this invention is shown in FIG. 1. As depicted, the assembly is an integrated catheter. It will be appreciated that aspects of the instant invention may be employed with other catheter and introducer needle assemblies, such as those disclosed in U.S. Pat. Nos. 4,326,519; 5,810,780; 5,935,110; 5,676,656; and 5,879,334, each incorporated herein by reference. In accord with one implementation of the invention, the catheter and introducer needle assembly includes catheter 20 affixed to catheter hub 21 and needle 40 affixed to needle hub 41. The catheter includes a central bore 120 having a cross sectional area and may be formed of translucent material (including transparent materials). As used herein, "translucent" materials shall be construed to include transparent materials, as well as materials that permit light to pass but not clearly enough to be deemed transparent.

The needle 40 has an outer diameter sized such that the cross sectional area of the needle is less than the cross sectional area of the central bore 120 of the catheter 20. Consequently, an annular space 60 (see FIG. 2A) is defined between the catheter and the needle. The needle also includes a central chamber 160 extending axially through the needle. As discussed below, the chamber is in fluid communication with a notch 42 in the needle.

Figure 2:
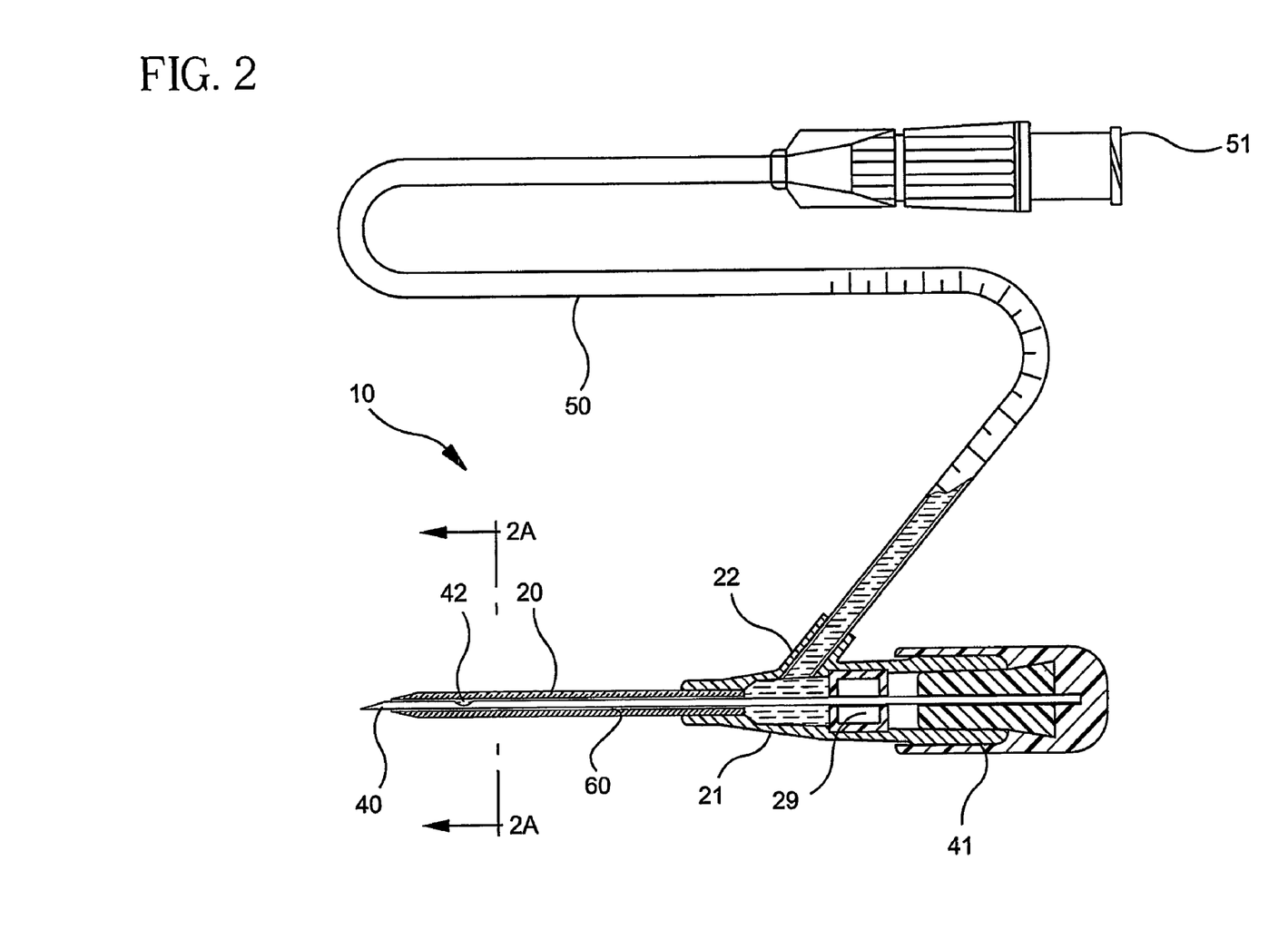
FIG. 2 is a cross-sectional view of the invention taken along line 2-2 in FIG. 1 showing the assembly prior to insertion into a patient with the needle in the forward position.
Figure 2A:
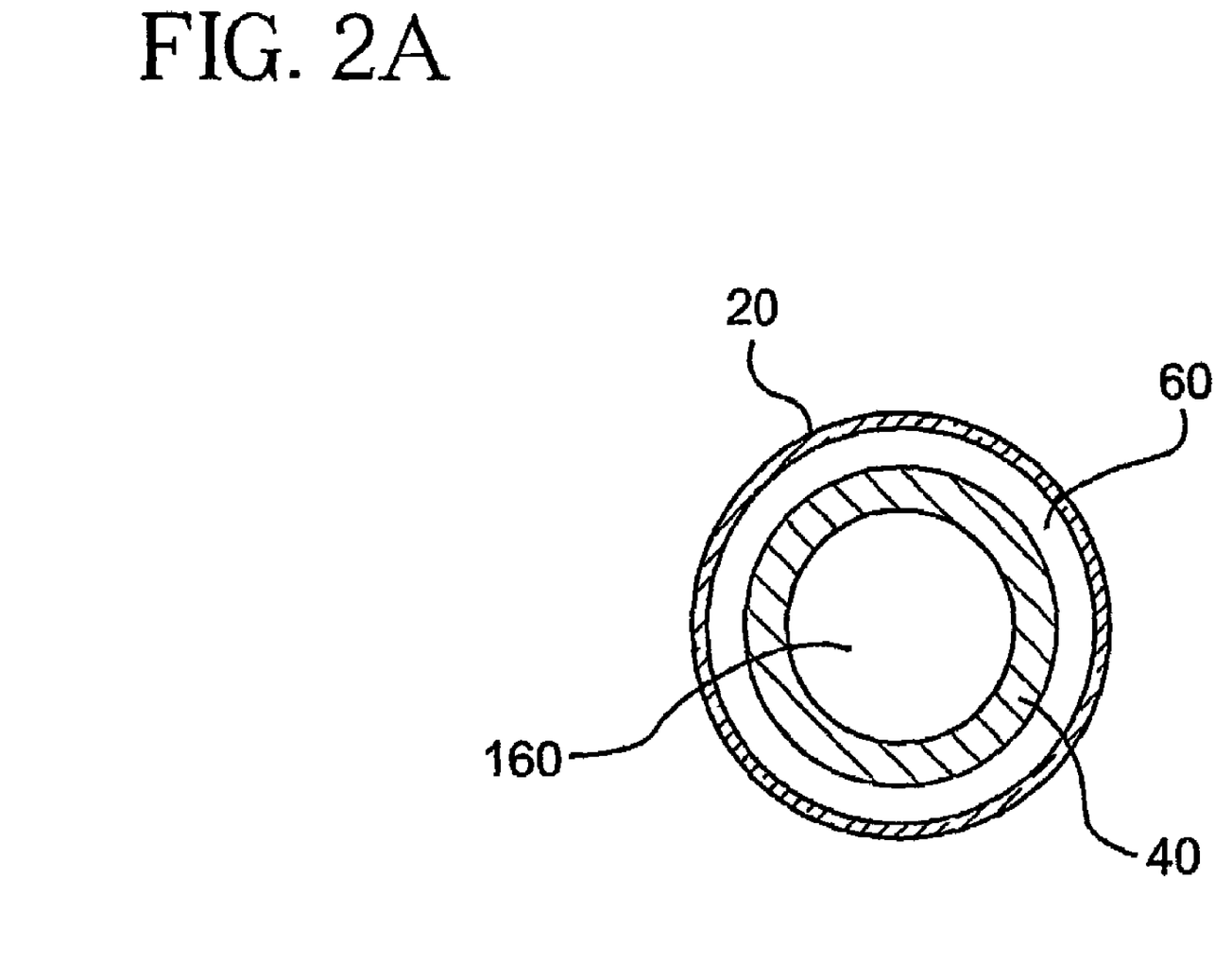
FIG. 2A is a cut-away view of the assembly taken along line 2A-2A of FIG. 2.

As shown in FIG. 2 before withdrawal of the needle 40 from the catheter assembly 10, the distal end of the catheter 20 seals about the needle 40, preventing distal flow of blood out of the catheter. Catheter hub 21 includes a side port 22 which has an extension tube 50 connected and in fluid communication with the catheter hub 21. The extension tube has a central chamber 54 and is made of a translucent material. Side port 22 is in fluid communication with the annular space 60 in the catheter 20 so that fluid infused through extension tube 50 will pass into the patient once catheter 20 is properly positioned in the patient (even if the needle is still in position in the catheter). Conversely, blood exiting a patient's vein through catheter 20 can travel through extension tube 50, whether the needle is still in the assembly 10, or not. Scale markings 55 may be provided to assist the caregiver appreciate the rate of blood flow through the extension tube, as discussed below.

The proximal end of extension tube 50 (that is, the end remote from the catheter hub) typically includes a standard luer lock adaptor 51 to allow the connection of an IV fluid supply line to extension tube 50. Such an IV fluid supply line can be connected to extension tube 50 prior to insertion of assembly 10 into a patient. The adaptor may include a plug 53 formed of a porous material, which permits the flow of air but prevents the passage of liquids, such as blood. As discussed below, the porosity of the material may be selected to control the flow rate of blood in the extension tube. In certain applications, the porosity of the material is selected to permit passage of 0.03 cubic centimeters of air per minute.

The proximal end of catheter hub 21 is sealed with an elastomeric plug 29 (see FIG. 2) to ensure that fluid does not leak out of the proximal end of catheter hub 21 once the needle is withdrawn. Plug 29 may be filled with gel, such as silicone gel. This gel would seal the hole left by needle 40 when it is removed from catheter hub 21. In addition, this gel would fill the notch 42 when needle 40 passes through plug 29. This would prevent fluid from leaking through the notch tube 50, including lower tube portion 26, connected thereto located toward the distal portion of catheter hub addition thereto, the plug 29 could be a septum having an axial length greater than the distance between the distal end of the opening at the tip of the needle and the proximal end of the notch, as disclosed in U.S. Pat. No. 6,506,181, incorporated herein by reference.

As the catheter and introducer needle assembly 10 is inserted into a vein, blood passes through the opening in the chamber 160 of the needle 40, through the distal notch 42 and into the annular space 60. When the catheter 20 is translucent or transparent, flashback of blood in needle 40 is then observed by the caregiver as the blood passes through the notch into the annular space, thereby giving an initial indication that the needle tip has successfully accessed the vein. This initial indication is at the distal end of the catheter, near the point of insertion into the patient—thus providing nearly immediate visual feedback without requiring the caregiver to divert his attention from the point of insertion. The caregiver may manipulate the needle tip (and thus the catheter) into a final desired location. Blood continues to flow through the annular space 60, to the needle hub 21, through the side port 22 and through the extension tube 50.

Figure 3:
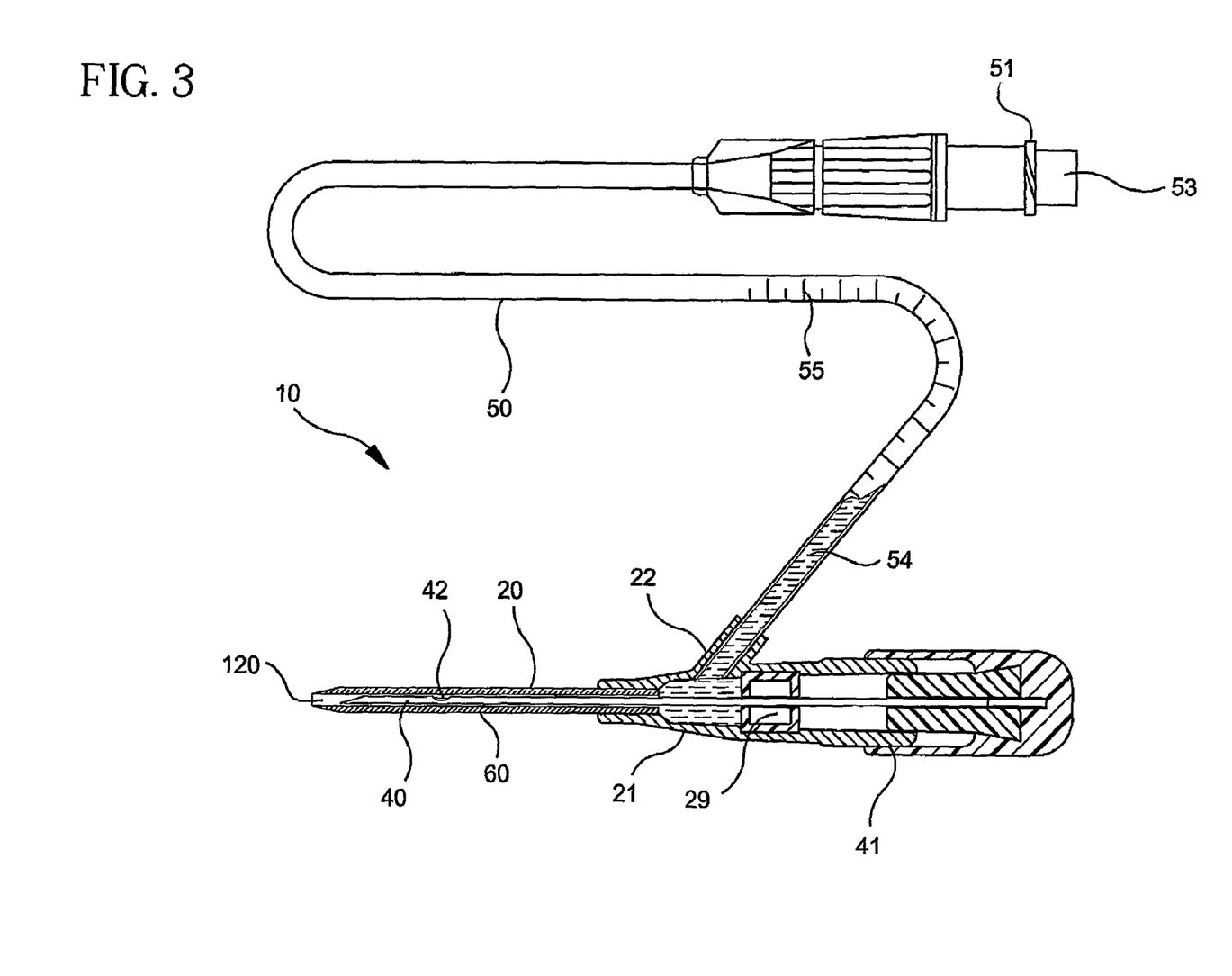
FIG. 3 is a cross-sectional view of the assembly of FIG. 1 with the needle in a retracted position.

Once the caregiver has positioned the catheter assembly 10 as desired, he can look at the extension tube 50 to confirm that the catheter tip is positioned within a vein. If properly located, flashback in the extension tube continues at the observable, controlled rate. The gauge markings 55 help the caregiver appreciate the rate of continued flow. Needle 40 can then be withdrawn from catheter hub 21 (see FIG. 3), leaving catheter 20 in place in the patient's vein. The observable confirmation flashback in the extension tube continues whether the needle is in place or not (at least until the extension tube 50 is filled with blood). Thus, the caregiver receives confirmation of proper catheter positioning even after the needle 40 is withdrawn.

In certain traditional devices, the only flashback is nearly immediate and complete from the initial access of the vein. Consequently, the flash chamber (which may be an annular space about the needle in the catheter, an extension tube or a distinct flash chamber) is filled with blood, preventing confirmation of venal access if the needle is moved. This is especially true when using needles having larger gauge sizes. In such cases, the flashback flow front may only be visible for a fraction of a second preventing a caregiver from receiving continued feedback (i.e., confirmation flashback) over an extended period of time. In accord with the instant application, however, the flow rate of blood through the catheter is controlled to permit continuous, active confirmation during a relatively long period of time despite the manipulation of the needle. Specifically, the size of the notch 42, the annular space 60 and the internal diameter of the extension tube 50 are selected to cause blood to fill the extension tube over a predetermined time. For example, these components may be sized to cause blood to fill the extension tube at a rate of at least 1 inch per minute when the blood is at 45 mmHg and has a viscosity of about 1.8 times that of water at 98.6 degrees F.

The extension tube preferably has a length of 4 inches. Consequently, it will take up to 4 minutes until the extension tube is filled with blood (at a minimum rate of 1" per minute). This allows the clinician a relatively long time to have confirmation flashback at a rate that is discernable. Such continuous, long term flashback also provides the caregiver information about the blood vessel accessed—such as whether it is a vein or an artery, whether there is pulsitile flow, the color of the blood, the pressure of the blood, and so on.

It is noted that the blood in the extension tube 50 may provide various observable characteristics to the caregiver, such as the visual flow front rate, the color of the blood, whether the visual flow front through the extension tube is pulsing, and so on. Consequently, a caregiver may be able to differentiate venous and arterial access by blood color (and flow rate) and by pulsitile flow. Indeed, characteristics of the blood vessel, such as blood pressure, may be observed by the flow rate of blood through the extension tube. Thus, aspects of the instant invention provide useful information to the caregiver beyond continued confirmation of venous access.

In accord with certain aspects of the invention, the geometry and material properties of the introducer needle and catheter assembly 10 may be "tuned" to achieve a desired visual flow front rate in the extension tube 50 based upon the gauge of the needle 40 to be employed. It is desirable that the visual flow front rate through the extension tube 50 be no less than 1 inch per minute. When it is determined that the annular space 60 shall be used as the throttle, the flow, or resistance to the flow of blood at a given pressure, in the introducer needle and catheter assembly is determined in part by three factors— the area of the annular space 60 between the catheter inner diameter and needle outer diameter, length of catheter 20, and viscosity of blood. The catheter 20 length is generally specified as part of the therapy that is needed (e.g., longer catheters to reach deeper veins and arteries) so that length must also be accommodated by adjusting the annular space 60 so that the proper confirmation flashback rate can be achieved in the extension tube. For example, a 20 gauge catheter, having a length of 1¾" may require the annular space be increased in size (compared to that of a shorter catheter) to achieve the desired visual flow front rate despite this length. This could be accomplished by reducing the outer diameter of the needle 40, thus increasing the area of the annular space 6 and the resulting confirmation visual flow front in the extension tube 50.

It is noted that, due to flow characteristics of fluids, as catheter 20 length increases, the area of the annular space must increase to maintain the same flow rate. Annular area/volume flow rate relationships can be established for different introducer needle and catheter assemblies. For example, 1.75" length catheters require a larger annular area to achieve the same minimum acceptable flow front rate in the extension tube 50 that would be able to be achieved with the shorter catheter lengths and a smaller annular area.

In the application of the invention discussed immediately above, the notch 42 and the needle chamber 160 are sized to have cross sectional areas greater than or equal to the cross sectional area of the annular space 60. Consequently, neither the notch nor the chamber act as a throttle and the volume rate of flow in the extension set can be controlled by controlling the size of the annular space (which, in turn, is defined by the outer diameter of the needle and the inner diameter of the catheter).

It is noted that, while depicted as a single rectangular cutout, the notch can be any shape, including circular, oval or the like. Further, the notch may be formed as a plurality of fenestrations in the needle wall.

Figure 4:
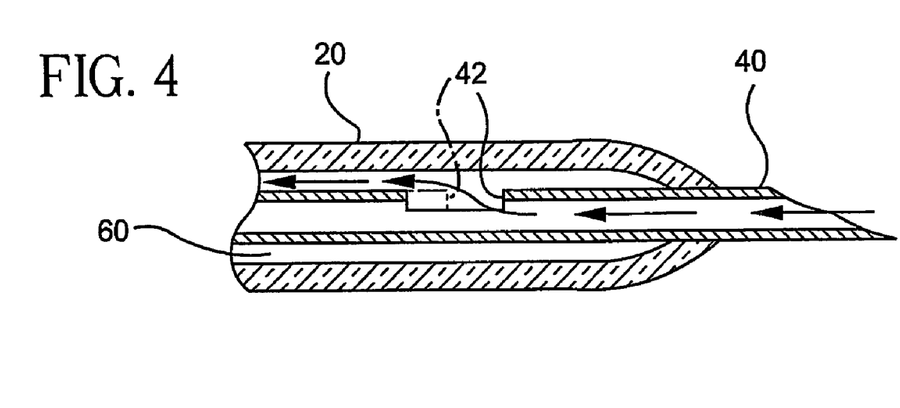
FIG. 4 is a cutaway side view of the distal tip of the needle and catheter with the needle in the forward position, depicting blood flow through the needle and catheter.
Figure 5:
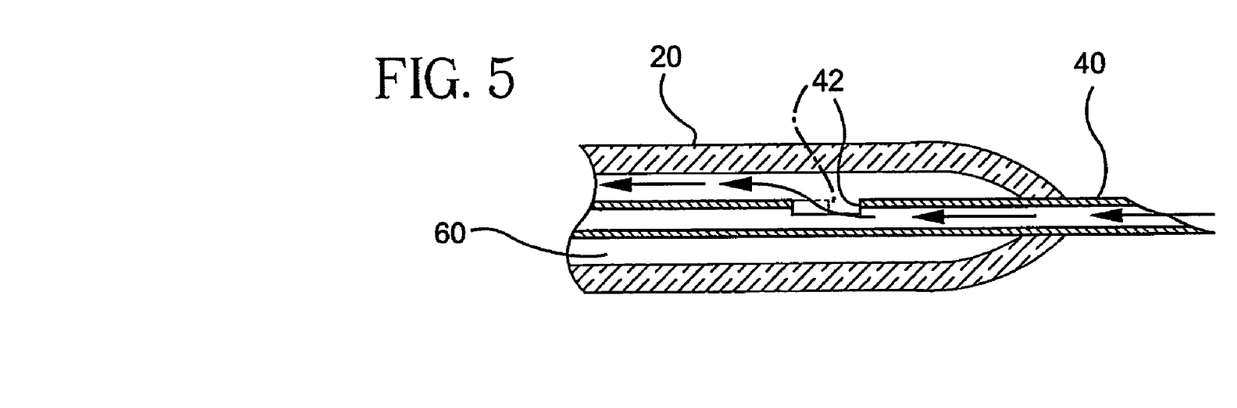
FIG. 5 is a cutaway side view of the distal tip of the needle and catheter with the needle in the forward position, depicting blood flow through the needle and catheter, and having an enlarged annular space.
Figure 6:
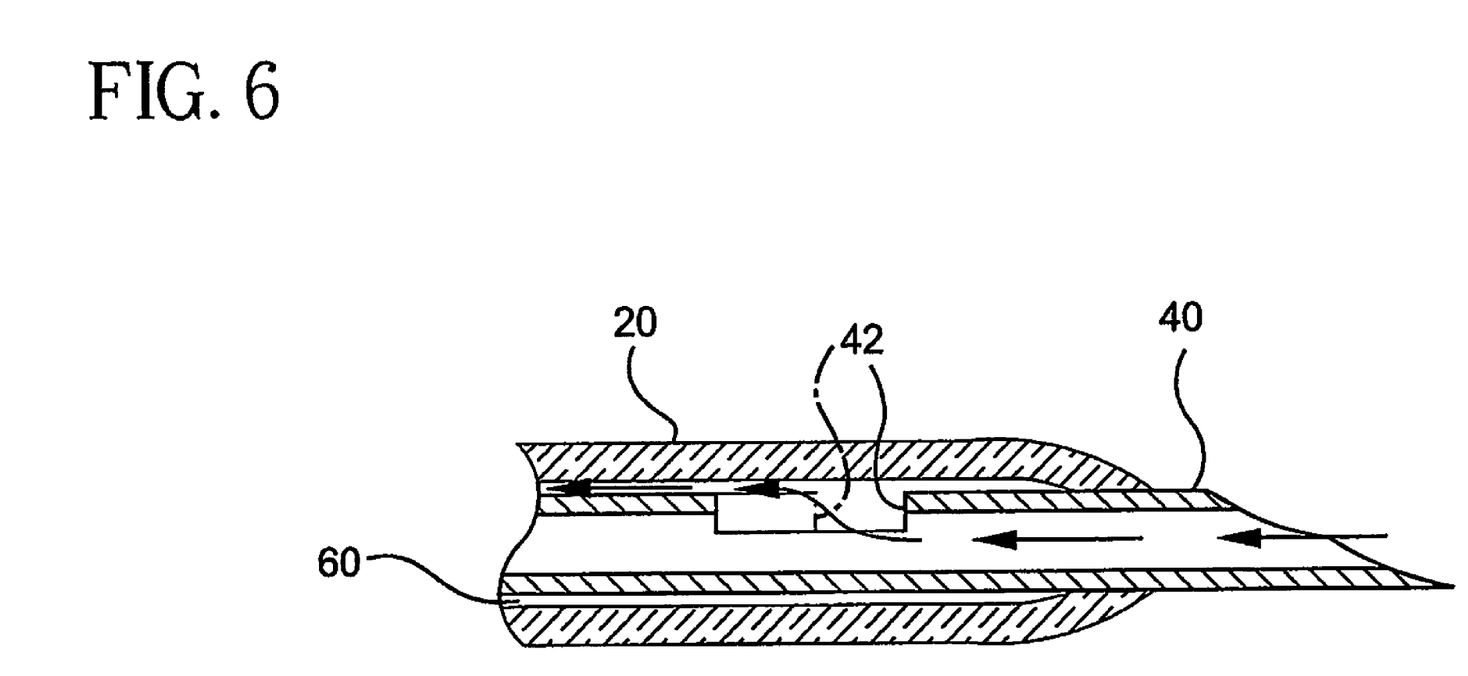
FIG. 6 is a cutaway side view of the distal tip of the needle and catheter with the needle in the forward position, depicting blood flow through the needle and catheter, and having a narrowed annular space.

Referring now to FIGS. 4-6, other implementations of the invention provide that the visual flow front rate through the extension tube 50 can be controlled by modifying the geometry of the needle 40 and catheter 20. Specifically, as seen in FIG. 4, when the notch is employed as the throttle, the size of the notch 42 can be modified. When the notch 42 is longer (resulting in a larger cross-sectional area), the flow rate through the needle and catheter assembly 10 increases, thereby increasing the visual flow front rate through the extension tube 50. As shown in phantom, when the notch 42 is shortened, flow rate through the needle and catheter assembly decreases, thereby decreasing the visual flow front rate through the extension tube.

Referring to FIG. 5, when the annular space 6 is employed as the throttle the annular space 60 can be increased (by using a needle 40 with a smaller outer diameter, a catheter 20 with a larger inner diameter, or both), thereby increasing flow rate through the needle and catheter assembly 10, and thus increasing the visual flow front rate through the extension tube 50. Conversely, the size of the annular space 60 can be decreased (see FIG. 6). As such, the flow rate through the needle and catheter assembly is decreased, and so too the visual flow front rate through the extension tube.

Thus, it is seen that an IV catheter and introducer needle assembly is provided that allows the healthcare worker to determine if the assembly is properly placed in a patient's vein without the need for the healthcare worker to divert his attention away from the insertion site and to confirm proper placement after positioning using controlled flashback in the extension tube (including confirmation after removal of the needle). Further, a method is provided for controlling flashback in the extension tube of an integrated catheter assembly. As such, the designer of such integrated catheters can ensure appropriate flashback rates, allowing the caregiver to observe continuous flashback over a selected period of time, depending upon the particular application. This control can be achieved by altering the size of the annular space between the needle and the catheter, the size of the notch in the needle, the size of the chamber extending through the needle, the size of the extension tube leading to the catheter adapter, the porosity of the filter plug in the extension tube, and any combinations of these.

I claim:

1. A method of controlling the fluid flow rate in an extension tube of an introducer needle assembly for confirmation flashback, the introducer needle assembly having a catheter attached to a catheter hub with a side port, an extension tube attached to the side port on the catheter hub at least a portion of which is translucent, and an introducer needle with a notch adapted to be inserted into a bore in the catheter, wherein the needle has an outer diameter smaller than the diameter of the bore such that an annular space is defined between the catheter and the needle, the method including:

selecting a preferred fluid flow front rate of a fluid through the extension tube, wherein the fluid is at a pressure and has a viscosity when it is accessed by the needle; and selecting a needle assembly from a plurality of needle assemblies capable of producing the preferred fluid flow front rate, wherein each needle assembly of the plurality of needle assemblies includes a distinct combination of needle assembly properties, including the sizing of the notch, the internal diameter of the extension tube, and the annular space, and wherein each distinct combination provides a distinct fluid flow rate through the extension tube based on the pressure and viscosity of the fluid when accessed by the needle.

2. The method of claim 1 wherein a porous material is located in the extension tube at a location remote from the side port, further including selecting the porosity of the material to achieve the preferred flow rate.

3. The method of claim 1 wherein the preferred fluid flow front rate is at least 1 inch per minute through the extension tube.

4. The method of claim 1 wherein the sizing of the notch is about 0.013 inch by 0.016 inch, the needle has an outer diameter of about 0.028 inch and the catheter has a bore with a diameter of 0.034 inch.

5. The method of claim 4 wherein the extension tube has an internal diameter of 0.05 inch.

6. The method of claim 5 wherein the fluid is at a pressure of about 30-50 mmHg and has a viscosity of 1.8 times that of water.

7. The method of claim 6 wherein sizing the notch and the annular space is based, at least in part, on the length of the catheter.

8. The method of claim 6 wherein a porous material is located in the extension tube at a location remote from the side port, further including selecting the porosity of the material to achieve the preferred flow rate.

9. The method of claim 1, wherein the introducer needle has a length and the catheter has a length, and wherein the needle assembly properties further includes the needle length and catheter length.

10. A method of accessing a blood vessel comprising:
selecting an introducer needle assembly from a plurality of introducer needle assemblies, the introducer needle assembly having a catheter attached to a catheter hub with a side port, an extension tube attached to the side port on the catheter hub at least a portion of which is translucent, and an introducer needle with a notch adapted to be inserted into the catheter such that the notch is disposed within the catheter;
inserting the tip of the introducer needle of the selected introducer needle assembly into the blood vessel;
confirming insertion of the introducer needle in the blood vessel by observing blood in the catheter near the notch;
positioning the tip of the catheter at a desired location within the blood vessel;
confirming positioning of the needle tip in the blood vessel by observing blood flow through the extension tube;
wherein the flow rate of blood through the extension tube is based upon, at least in part, a combination of the size of the notch, the size of the internal diameter of the extension tube and the outer diameter of the needle;
wherein each introducer needle assembly of the plurality of introducer needle assemblies includes a distinct combination of the sizing of the notch, the internal diameter of the extension tube, and the outer diameter of the needle, and wherein each distinct combination provides a distinct fluid flow rate through the extension tube, and wherein the selected introducer needle assembly is selected to achieve a desired visual flow front rate through the extension tube.

11. The method of claim 10 further including selecting the introducer needle assembly based, at least in part, on the pressure of the blood and the viscosity of the blood.

12. The method of claim 11 wherein the desired visual flow front rate through the extension tube is at least 1 inch per minute.

13. A method of providing a needle assembly designed to control flashback in an extension tube of the introducer needle assembly by limiting fluid flow through the extension tube to a predetermined, visual flow front rate, including:
providing a translucent catheter having a proximal end, a distal end and a central bore extending from the proximal end to the distal end, wherein the bore has a cross sectional area, wherein the translucent catheter is selected from a plurality of catheters each having different cross sectional areas;
providing a catheter hub in fluid communication with the central bore and having a proximal end and a distal end connected to the proximal end of the catheter and a side port in fluid communication with the catheter hub;
providing an extension tube in fluid communication with the side port at least a portion of which is translucent, wherein the extension tube is selected from a plurality of extension tubes each having a different internal diameter;
providing a seal affixed to the catheter hub and located proximal of the side port, the seal sealing the proximal end of the catheter hub;
providing an introducer needle having a proximal end and a distal end, and having a needle hub having a distal end and a proximal end, the proximal end of the introducer needle connected to the distal end of the needle hub, the introducer needle adapted to be positioned within the catheter in an insertion position wherein the distal end of the introducer needle extends distally past the distal end of the catheter;
the introducer needle having a cross sectional area that is less than the cross sectional area of the central bore such that an annular space is defined between the introducer needle and the catheter;
providing a notch at the distal end of the introducer needle located within the catheter when the introducer needle is in the insertion position such that fluid can communicate between the notch at the distal end of the introducer needle and the side port but is prevented from passing out of the proximal end of the catheter hub by the seal;
wherein the introducer needle is selected from a plurality of introducer needles each having a different combination of cross sectional area, cross sectional area of the central bore, and notch size,
wherein the selected introducer needle, extension tube and catheter, in combination, control the flow of fluid through the extension tube such that a controlled visual flow front rate is established through the extension tube.

14. The method of claim 13 wherein the notch has an area of about 0.0002 inches$^2$, the annular space is about 0.0012 inches$^2$, the extension tube has an internal diameter of 0.05 inches, the fluid is at 30-50 mmHg and has a viscosity of about 1.8 times that of water.

15. The method of claim 13, wherein the seal includes a gel.

* * * * *